(12) United States Patent
Heithecker et al.

(10) Patent No.: US 8,501,720 B2
(45) Date of Patent: Aug. 6, 2013

(54) METHOD FOR TREATMENT OF DYSMENORRHEA

(75) Inventors: Renate Heithecker, Berlin (DE); Bernd Duesterberg, Oberkraemer (DE)

(73) Assignee: Bayer Pharma AG, Berlin (DE)

( * ) Notice: Subject to any disclaimer, the term of this patent is extended or adjusted under 35 U.S.C. 154(b) by 311 days.

(21) Appl. No.: 11/193,617

(22) Filed: Aug. 1, 2005

(65) Prior Publication Data

US 2006/0128679 A1 Jun. 15, 2006

Related U.S. Application Data

(60) Provisional application No. 60/592,122, filed on Jul. 30, 2004.

(51) Int. Cl.
*A61K 31/56* (2006.01)
(52) U.S. Cl.
USPC .......................................... 514/170; 514/171
(58) Field of Classification Search
USPC .................................. 514/171, 170
See application file for complete search history.

(56) References Cited

U.S. PATENT DOCUMENTS

| | | | | |
|---|---|---|---|---|
| 5,898,032 | A | * | 4/1999 | Hodgen ........................ 514/178 |
| RE37,564 | E | * | 2/2002 | Spona et al. .................. 514/170 |
| 6,500,814 | B1 | | 12/2002 | Hesch |
| 2003/0018018 | A1 | * | 1/2003 | Hodgen et al. ................ 514/171 |

FOREIGN PATENT DOCUMENTS

EP 1 275 394 A2 1/2003

OTHER PUBLICATIONS

Fraser et al., MJA, 2003;178(12):621-623.*
Apter et al., European Journal of Contraception and Reproductive Health Care, 2003;8:37-51.*

* cited by examiner

*Primary Examiner* — San-Ming Hui
(74) *Attorney, Agent, or Firm* — Millen, White, Zelano, Branigan, P.C.

(57) ABSTRACT

A method of treatment of dysmenorrhea in the context of oral contraception characterized by daily administration of ethinylestradiol and drospirenone in an extended regimen.

8 Claims, 4 Drawing Sheets

METHOD FOR TREATMENT OF DYSMENORRHEA

Figure 1:
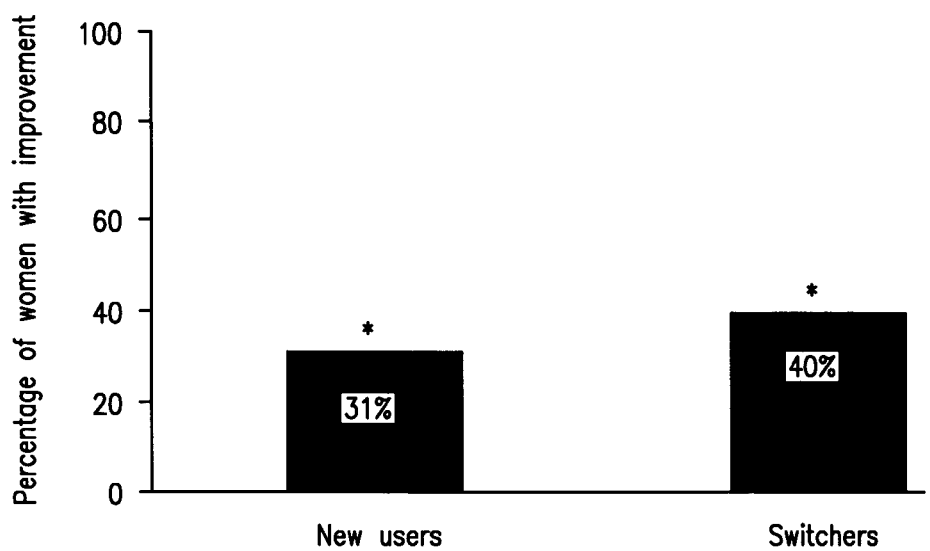

This application claims the benefit of the filing date of U.S. Provisional Application Ser. No. 60/592,122 filed Jul. 30, 2004.

The present invention relates to a method of treatment of dysmenorrhea in the context of oral conception.

The oral contraceptive to be used in the method of the invention is characterized by containing ethinylestradiol as the estrogen and drospirenone as the progestin.

The daily amount of ethinylestradiol to be administered is in the range of 15 µg to 30 µg, preferably 20 µg to 30 µg.

The daily amount of drospirenone to be administered is in the range of 2 µg to 4 mg, preferably 3 mg.

The method is further characterized by the administration of the oral contraceptive in a so-called extended use regimen, i. e. the oral contraceptive is administered daily and uninterruptedly without making the conventional pill break of 7 days or without administration of 7 placebos after the administration of 21 daily dosage units containing an estrogen and a progestin (21+7 regimen).

According to the invention daily administration of the oral contraceptive for 84 days followed by 7 days of non-administrative (either 7 pill-free days or administration of 7 placebos) is preferred. Such administration regime is described in U.S. Pat. No. 5,898,032 B. It leads to 4 "menstruation cycles" per year.

The invention also pertains to longer uninterrupted daily administration of the oral contraceptive to treat the symptoms of dysmenorrhea, e. g. administration for more than 110 days or even more than one year. Respective regimes for oral contraception are described in the prior art, e.g. U.S. Pat. No. 6,500,814 B1 and EP 1 275 394 A2, respectively.

All these prior art documents do not relate to drospirenone as the progestin and they do not teach the favorable influence of the extended use regimens compared to the conventional (21-7)-regimens in treating the symptoms of dysmenorrhea.

Details how to perform the present invention and advantages of the present invention become apparent from the study described below using the (84+7)-regimen with daily administration of 30 µg ethinylestradiol and 3 mg drospirenone.

The reduction in dysmenorrhea is significantly higher after treatment of 6 months in patients using the extended regimen than in patients using the "classical" (21+7)-regimen.

The advantages of the invention are not limited to reducing dysmenorrhea. Also other symptoms and conditions can be influenced favorably under extended use of an ethinylestradiol/drospirenone containing oral contraceptive compared to 1 st conventional (21+7) administration.

ABSTRACT

As well as providing reliable contaceptive, modern low-dose oral contraceptives may offer some non-contraceptive advantages. Positive effects on problems such as edema with weight increase and breast tenderness, bloating, dysmenorrhea, and an improvement in skin and hair condition have been reported in several studies using an oral contraceptive containing drospirenone. If these disorders are cycle-dependent, use of the contraceptive in long-term cycles may be of addition benefit. The study reported in this paper followed 1433 women, 175 of whom took the dorspirenone-containing pill continuously for between 42 and 126 days. Some symptoms of the premenstrual syndrome were influenced very satifactorily by long-cycle administration.

INTRODUCTION

Progestogens in combination with ethinylestradiol provide reliable inhibition of ovulation, with the estrogen component giving good cycle control. The extensive choice of progestogens available, with different pharmacological properties allows contraception that may suit individuals and is well tolerated, by each woman. By exploiting the partial effects of the progestogens, additional favorable effects may also be gained, for example, the specific antiandrogenic properties of cyproterone acetate, dienogest, drospirenone, and chlormadinone acetate, on the skin and hair.

With the introduction of drospirenone to oral contraception, it is now possible for the first time to counteract specific disorders associated with water retention. Relevant antimineralocorticoid effects have previously been demonstrated only for progesterone. The potential to counteract estrogen-induced water retention by constant dosage reduction is limited, since this can result in breakthrough bleeding, as shown by the development of contraceptive pills containing less than 30 µg ethinylestradiol. The oral contraceptive tested here contains 30 µg ethinylestradiol, a dose which is suitable for the majority of women, combined with 3 mg drospirenone. This dose ensures reliable inhibition of ovulation and, at the same time, exhibits antiandrogenic and mild antimineralocorticoid activity[1].

An improvement in cycle-dependent disorders, such as breast tenderness, edema, bloating and skin changes, together with some psychological symptoms, such as fatigue and depressive mood, has been demonstrated with the conventional use of the contraceptive pill containing drospirenone in a 21-day 'monthly' cycle. This favorable effect can be enhanced by omitting the hormone-free interval ('long' cycle), with troublesome withdrawal bleeding reduced for many women. As a number of different studies with other preparations have already shown, cycles of 2-3 months lead to only slight breakthrough bleeding with regular withdrawal bleeding episodes; these tend to be weak and occur in the pill-free interval[2]. The regimen is only suitable, however, for single-phase preparations, i.e. those with a constant progestogen dose. It is frequently possible, by inducing 'iatrogenic amenorrhea', for the symptoms of dysmenorrhea to be reduced or eliminated altogether[2].

The approval studies[3,4] for the ethinylestradiol/drospirenone combination in a 21-day monthly cycle showed a positive influence, in particular, on the cycle-dependent disorders of water retention and symptoms of premenstrual syndrome. Since body weight remained stable or was slightly reduced, and skin problems, such as acne and seborrhea, perceptibly improved, it was a logical consequence to test the same pill in a long-cycle regimen. The aim was to determine whether the positive effects induced by the antimineralocorticoid and antiandrogenic activity could be further enhanced.

PATIENTS AND METHODS

A total of 1433 women were prescribed the oral contraceptive containing 3 mg drospirenone and 30 µg ethinylestradiol for the first time in the period between February and October 2002. The study was notified to the German Federal Institute for Pharmaceutical and Medical Products in accordance with German Pharmaceutical and Medical Products Law. These women were observed prospectively for 6 months by 152 gynecologists, both male and female. No arrangements for blinding were made.

A comparison was made between 668 women (47%) who had not taken any other preparation previously (new users), and 765 women (53%) who were changing from another preparation to the test preparation (switchers).

Some women were asked to take the preparation in a different protocol to the mode of administration specified in the application instructions (in accordance with the usual administration of 21 days taking the pill and a 7-day pill-free interval). In total, 175 women took the preparation on the basis of an individual prescription from their gynecologist in what is referred to as the 'long' cycle (without an interval, over a period from 42 to 126 days). These 175 women were compared with 1221 users on a monthly cycle.

The following data were collected and entered online into a databank, first at the time of admission to the study, and after 6 months:
(1) Swelling of the extremities;
(2) Body weight;
(3) Breast tenderness;
(4) Feeling of bloating;
(5) Condition of the skin;
(6) Dysmenorrhea;
(7) Breakthrough bleeding, and
(8) Withdrawal bleeding.

In addition to this, at the final examination, the subjects were questioned about their satisfaction with the therapy. Undesirable side-effects were collated according to body system, in accordance with the WHO-ART classification, Statistical Analysis For the descriptive statistical evaluation, the single sample t test and Fisher's exact test were used. To assess the change in the subjective symptoms, it was determined for each woman whether the symptoms:
(1) Had improved (date of admission: symptoms present; last documented status: not present);
(2) Had remained the same (date of admission: symptoms present; last documented status: present; or date of admission: symptoms not present; last documented status: not present);
(3) Had become worse (date of admission: symptoms not present; last documented status; present).

The significance level was determined at $p<0.05$.

Results

Effect on Water Balance (Edema and Weight)

Figure 2:
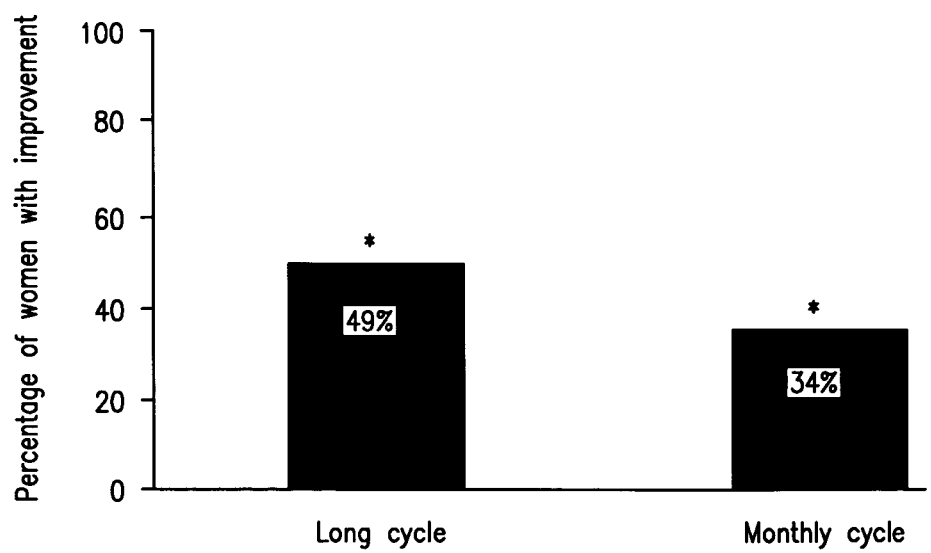

Relative to the group as a whole, 31% of the new users showed a reduction and 4% an increase in edema, as opposed to 40% and 2%, respectively of the switchers. The difference between these two groups was significant ($p<0.05$) (FIG. 1). Swelling of the extremities improved in the women on the long cycle at 49%, and became worse among 2%. In the women on the monthly cycle, the rates were 34% and 3%, respectively. The difference between these two groups was significant ($p<0.001$) (FIG. 2).

During the administration of the test preparation, there was a mean decrease in weight among the group as a whole of 0.6 kg ($p<0.0001$). Among new users, a significant mean weight reduction of 0.44 kg was demonstrated ($p<0.0001$). Among switchers, there was likewise a significant mean weight reduction of 0.74 kg ($p<0.0001$). Among long-cycle users, the mean weight reduction amounted to 0.57 kg ($p<0.0001$), and, among monthly-cycle users, 0.61 kg ($p=0.0042$). The difference between these two groups was not significant.

Reduction of Breast Tenderness With the Long-cycle Regimen

Figure 3:
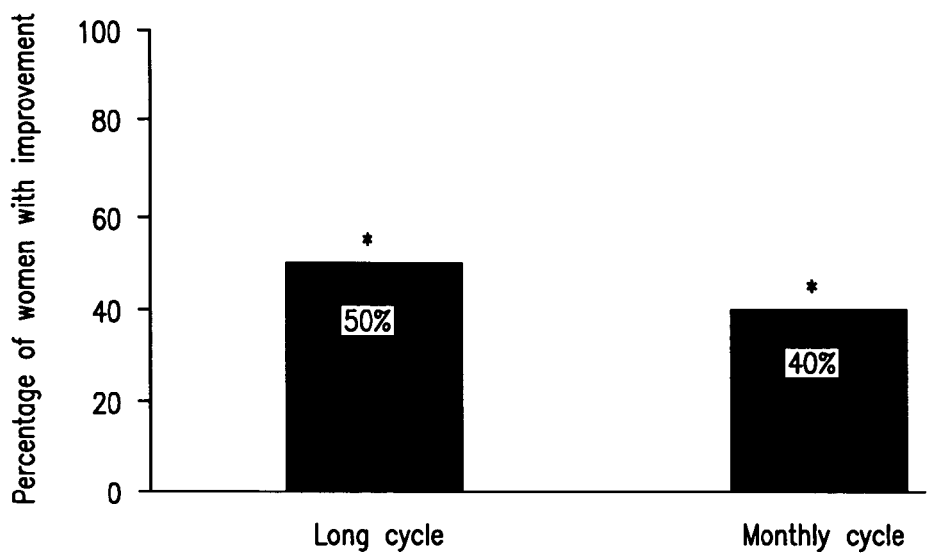

Breast tenderness improved in the group as a whole, by 40% among new users and by 42% among switchers. There was an improvement in this symptom among 50% of the long-cycle users, and 5% showed deterioration, compared with 40% improvement and 7% deterioration in the monthly-cycle users. The difference between these two groups was significant ($p=0.05$) (FIG. 3).

Reduction of Feeling of Bloating

Figure 4:
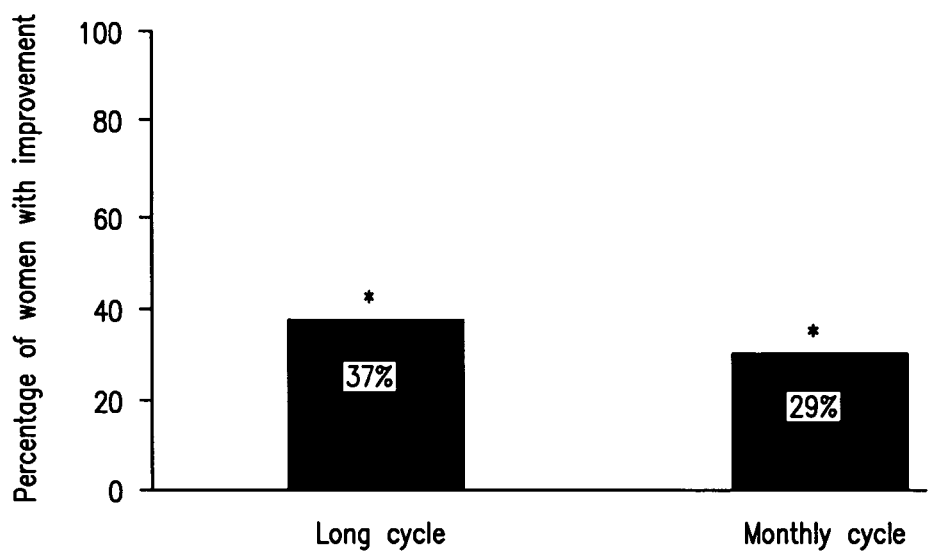

With regard to a feeling of bloating, an improvement was demonstrated of 31% among new users, and 30% among switchers. These symptoms improved among 37% of long-cycle users and 29% of monthly-cycle users. There were no significant differences between long-cycle and monthly-cycle users (FIG. 4).

Improvement in Skin Problems

Figure 5:
Figure 6:
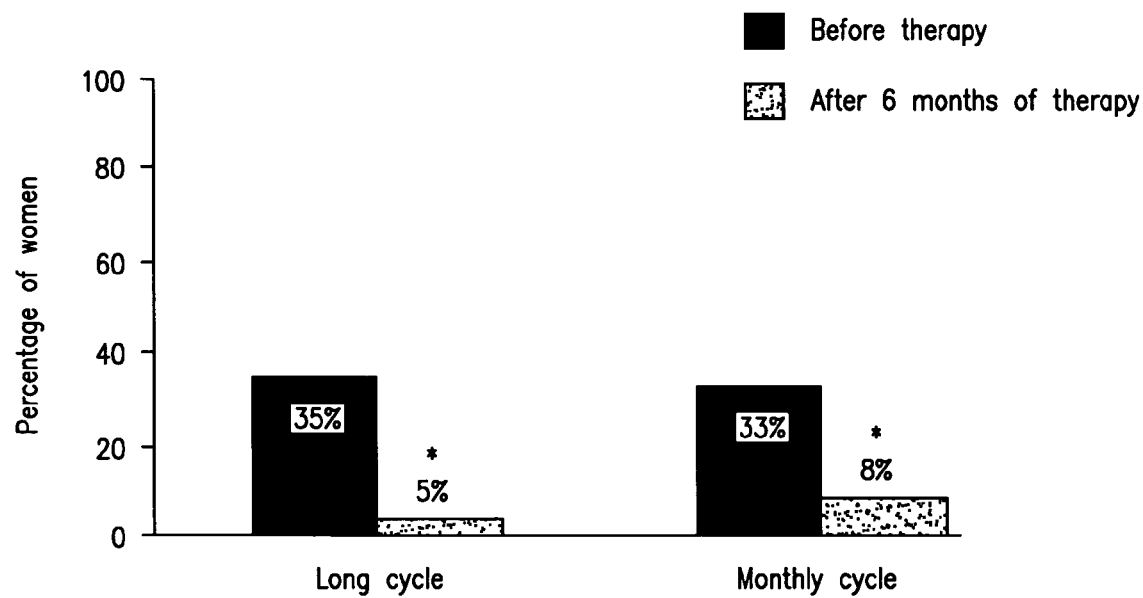

Moderate or severe skin problems were observed at the start of the therapy in 35% of new users and 32% of switchers, in relation to the group as a whole. These figures were reduced after 6 months to 8% and 7%, respectively (FIG. 5). At the start of the therapy, 35% of long-cycle users and 33% of the monthly-cycle users complained of moderate and severe skin problems. These figures were reduced to 5% and 8%, respectively, after 6 months (FIG. 6).

Improvement in Dysmenorrhea

Figure 7:
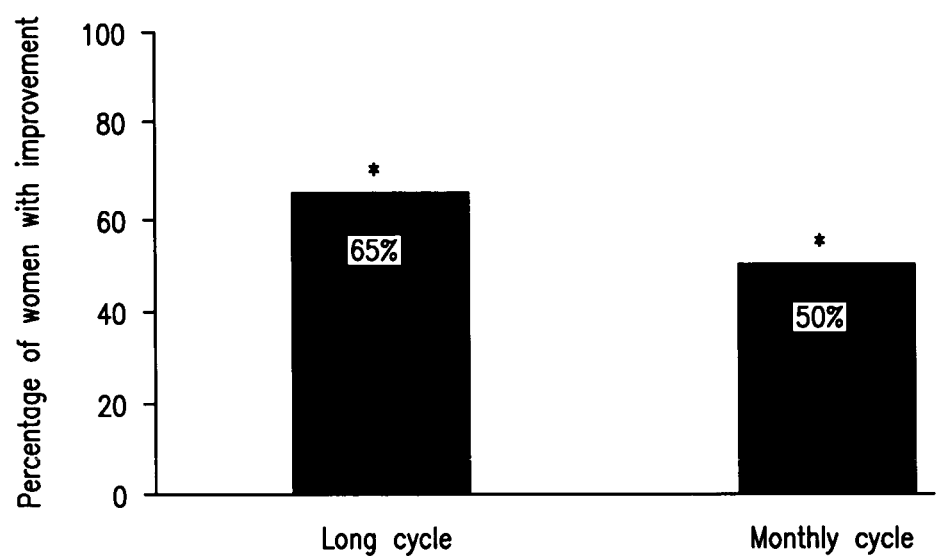

With regard to dysmenorrhea, there was a significant improvement after 6 months among 59% of the new users, and 10% reported a deterioration in relation to the period before administration, compared with a 46% improvement and 4% deterioration among switchers (difference between the groups, $p=0.0001$). In comparison with long-cycle and monthly-cycle administration, at 65% versus 50% improvement, and 2% versus 3%, there is a significant advantage in favor of long-cycle administration ($p=0.0016$) (FIG. 7).

Bleeding Behavior

In the long cycle, breakthrough bleeding occurred 15% more frequently than with monthly-cycle administration (6%). Withdrawal bleeding after long-cycle administration did not differ in terms of duration and severity from the monthly-cycle administration.

Undesirable Side-effects

Minor undesirable side-effects, such as headaches, were reported in 1.9% of women, with no difference in the subgroups; serious side-effects were not observed during the administration period.

Increase in Well-being Resulting From Long-cycle Administration

By comparison with the group as a whole, 68% of new users indicated that they felt better or much better, as opposed to 70% of switchers, and 2% and 4%, respectively felt worse or much worse (not significant). After 6 months, 85% of the long-cycle users felt better than at the beginning, and 2% worse. No patient reported feeling much worse. Among monthly-cycle users, 66% felt better and 3% worse ($p<0.0001$).

Further Recommendation

In the group as a whole, 93% of the new users and 91% of switchers, as well as 97% of the long-cycle users and 91% of the monthly-cycle users, recommended the preparation.

Discussion

Positive effects of the oral contraceptive containing drospirenone on symptoms of water retention and the appearance of the skin have been reported previously and were confirmed in the present study of 1433 women[3,4]. The high number of participants in the study, in particular of the long-cycle users (more than 10% of the group as a whole) emphasizes the significance of this study, despite the known reservations from observational studies.

An Active Substance With Partial Antiandrogenic and Antimineralocorticoid Effects Drospirenone owes its pharmacological profile to its molecular structure, derived from 17α-spirolactone. As well as its progesterone-like effect, the compound exhibits partial antimineralocorticoid and antiandrogenic effects[5]. The antiandrogenic properties are present at approximately one-third of the effective strength cyproterone acetate[5], and exceed those of chlormadinone acetate, in the conventionally used and standardized Hershberger test. In the present study, an improvement in skin conditions was also observed among the switchers, who had changed to the preparation from other oral contraceptives having some antiandrogenic effect.

The antimineralocorticoid effect is derived from the direct competition of drospirenone with aldosterone for binding to the aldosterone receptor. With women having a predisposition to water retention and edema, associated with 'heavy legs', breast tenderness, and weight increase, a reduction in water retention due to the specific antimineralocorticoid effect of drospirenone may be of clinical relevance, as the results of the present study suggest.

Interference in Mineralocorticoid Metabolism and Premenstrual Syndrome

Increased stimulation of the renin-angiotensin-aldosterone system (RAAS) (causing water retention) is possible if the effect of estrogen, incurred primarily by increased production of the hepatic angiotensinogen, is inadequately balanced by a reduced level of progesterone (luteal phase insufficiency). This is frequently observed not only among adolescents but also among older women. This imbalance is also relevant, inter alia, for the pathogenesis of premenstrual syndrome (PMS), in which symptoms of water retention are frequently observed.

The term PMS is used to describe a complex of symptoms from which some two-thirds of all menstruating women suffer[6]. In addition to physical disorders such as breast tenderness, feeling of bloating, edema, psychological symptoms of irritability and passive or aggressive depression play an important role, as well as attacks of bulimia. The pathogenesis of PMAS has not yet been fully explained. It is true that the symptoms are unambiguously cycle-dependent, but the peripheral hormone values are not striking in any reproducible manner. By contrast, there is considerable support for a genetic component as well as for an abnormal reaction of the serotoninergic system to normal cyclic hormone fluctuations[7].

The results of this study also provide indications that, in the pathogenesis of PMS, interferences in the mineralcorticoid metabolism must be of significance, since women who had previously used another oral contraceptive benefited to at least the same degree as new users. With regard to the symptom of 'swelling of the extremities', the improvement among women who changed from another pill was even more clearly marked.

These effects can be clearly demonstrated in a long cycle. For example, in the present study, there was, a significant reduction of edema and breast tenderness among long-cycle users in comparison with the women on the conventional 21-day monthly cycle. Thus, in the event of these symptoms being present, a regimen of 42-126 days could be recommended. There are no grounds for anticipating an accumulation of drospirenone; the half-life of the substance is about 27 h[8], and, according to the conventional rules of pharmacokinetics, a steady state is attained after about four half-lives, i.e. after at most a week, so that the level of drospirenone should not differ in conventional and in extended cycles.

Less Frequent Episodes of Bleeding Regarded as Positive by Many Patients

While amenorrhea induced by oral contraceptives has been previously regarded as undesirable, more recent studies show that many women would prefer no withdrawal bleeding or 3-monthly menstrual periods[9]. Long cycles do not, as a rule, give rise to expectations of either over-stimulation of the endometrium or increased withdrawal bleeding. The formation of endogenous estradiol is suppressed and ethinylestradiol has a comparably minor effect on the endometrium[10]. Due to the longer administration of drospirenone over several months, the endometrium becomes more markedly atrophied. Examination of the endometrium after conventional administration of the preparation after 6 months produced a diagnosis of atrophied endometrium[11] in 44% of the women, and in 63% after 13 cycles.

This effect is also to be anticipated from the long-cycle administration, with the result that the episodes of breakthrough bleeding are rarely intense in comparison with the conventional cycles. Initial frequent breakthrough bleeding can be explained by individual hormonal balance, where unstable conditions in the endometrium are replaced by the long-term effect of a fixed estrogen/progestogen combination and adequate atrophization is reached. In contrast, however, when even long-term administration of the pill is suspended, the immediate recurrence of endogenous estradiol secretion means that endometrium proliferation and fertility are not affected.

Further Advantages of the Long-cycle Regimen

Among the greatest advantages of the long-cycle regimen is the positive effect on dysmenorrhea. An improvement in dysmenorrhea with the test preparation in the monthly cycle has already been demonstrated in earlier studies. In the present study, a reduction of dysmenorrhea in the monthly cycle has been confirmed. With the long-cycle administration, the improvement in dysmenorrhea was even more marked than with the monthly-cycle application.

A further advantage of longer cycles, largely unrecognized, derives from the balance achieved in the metabolic parameters, which, when adjusted under the influence of oral contraceptives, are not changed every 3 weeks. For certain systems, such as coagulation/fibrinolysis, or vasolonic effects, corresponding negative changes may take place as early as during the 1-week pill-free intervals[13]. This probably only occurs among women with a predisposition, however, or in the presence of existing pathological changes of clinical significance, since healthy systems normally react adequately to changes.

In part, however, the frequent cyclic migraine-like disorders with vasotonic changes, caused by the abrupt withdrawal of the estrogen, can also be linked to this ('estrogen withdrawal migraine'); it is also possible, however, that the progestogen withdrawal has a part to play[14], These forms of 'menstrual migraine' can be treated by the administration of the long-cycle regimen. Further medical reasons for long cycles or iatrogenous amenorrhea, not examined in the present study, are iron deficiency anemia, endometriosis, and polycystic ovaries.

The more frequent breakthrough bleeding with long-cycle administration evidently did not have any effect on the positive overall evaluation by the long-cycle users. In the present study, breakthrough bleeding showed a tendency to decrease in frequency and intensity during the 6-month administration. An important factor in the increase in compliance is that the women were advised that spotting, if not attributable to missed pills, was not associated with a loss of contraceptive effect. In most cases, the induction of a regular withdrawal bleeding episode by the imposition of a 1-week break in administration resolved the problem.

Women choosing to take the long-cycle administration have to be informed that no unwelcome effects are to be expected from the long-cycle administration with regard to health and fertility, and, in particular, that the absence of 'monthly bleeding', provided that the long-cycle scheme is correctly maintained, is not an indication of pregnancy.

Almost All Users Recommend Long-cycle Administration

In summary, the present study shows that a long-cycle administration of the combination of 30 µg ethinylestradiol with 3 mg drospirenone can further enhance the possible therapeutic effects provided by the antimineralocorticoid activity (improvement of breast tenderness, edema, bloating), and the antiandrogenic activity (positive effects on the skin). This long-cycle administration was favorably assessed by the users with good tolerance evident from the observation that 97% of long-cycle users recommend this administration regimen to others.

References

1. Muhn P, Krattenmacher R, Beier S, et al. A novel progestogen with antimineralocorticoid and antiandrogenic activity. *Contraception* 1995;51:99-110
2. Clarke A K. Miller S J. The debate regarding continuous use of oral contraceptives. *Ann Pharmacother* 2001;35; 1480-4
3. Brown C, Ling F. Wan J. A new monophasic oral contraceptive containing drospirenone effect on premenstrual symptoms. *J Reprod Med* 2002;47:14-22
4. Apter D, Borsos A, Baumgärtner W. et al. Effect of an oral contraceptive containing drospirenone and ethinylestradiol on general well-being and fluid-related symptoms. *Eur J Contracept Reprod Health Care* 2003;8:37-51
5. Fuhrmann U, Krattenmacher R, Slater E P, et al. The novel progestin drospirenone and its natural counterpart progesterone: biochemical profile and antiandrogenic potential. *Contraception* 1996;54:243-51
6. Singh B B, Berman B M, Simpson R L, et al. Incidence of premenstrual syndrome and remedy usage: a national probability sample study. *Altern Ther Health Med* 1998;3: 75-9
7. Joffe H, Cohen L S. Estrogen, serotonin and mood disturbance: where is the therapeutic bridge? *Biol Psychiatry* 1998;44:798-811
8. Krattenmacher R. Drospirenone: pharmacology and pharmacokinetics of a unique progestogen. *Contraception* 2000;62:29-38
9. Glasier A F. Smith K S, van der Spuy Z M, et al. Amenorrhea associated with contraception—an international study on acceptability. *Contraception* 2003;67:1-8
10. Brosens I A, Pijenenborg R. Comparative study of the oestrogenic effect of ethinylestradiol and mestranol on the endometrium. *Contraception* 1976;14:679-85
11. Lüdicke F, Johannisson E, Helmerhorst F M, et al. Effect of a combined oral contraceptive containing 3 mg of drospirenone and 30 µg of ethinylestradiol on the human endometrium. *Fertil Steril* 2001;76:102-7
12. Foidart J-M, Wuttke W. Bouw G M, et al. A comparative investigation of contraceptive reliability, cycle control and tolerance of two monophasic oral contraceptives containing either drospirenone or desogestrel. *Eur J Contracept Reprod Health Care* 200;5:124-34
13. Mueck A G, Römer T. Stoffwechsel und Hormonsubstitution. Stuttgart: Thieme, 2002:56-64; 95102; 167-71
14. Reiners K. Zur Problematik der zyklusabhängigen Migräne. *Gynäkologe* 1989:22:326-31

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure of all applications, patents and publications, cited herein and of corresponding U.S. Provisional Application Ser. No. 60/592,122, filed Jul. 30, 2004 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

FIG. 1 Decrease in edema in both groups after 6 months. There was a significantly higher reduction in edema among switchers in comparison with new users FIG. 2 Significantly higher reduction in edema after 6 months in long-cycle users in comparison with monthly-cycle users FIG. 3 Significant improvement in breast tenderness in each group after 6 months. In the long-cycle users, this improvement was significantly higher than in the monthly-cycle users FIG. 4 Significant improvement in bloating in each group after 6 months. The difference between long-cycle users versus monthly-cycle users was not significant FIG. 5 Significant improvement in skin problems after 6 months among both new users and switchers FIG. 6 Significant improvement in skin problems after 6 months with both long-cycle users and monthly-cycle users FIG. 7 Significant reduction in dysmenorrhea after 6 months in each group. With long-cycle users, this reduction was significantly higher than with monthly-cycle users

The invention claimed is:

1. A method for reducing dysmenorrhea by administering 20 µg ethinylestradiol and drospirenone in a daily extended regimen uninterruptedly for 42-126 days.

2. A method according to claim 1 wherein the daily amount of drospirenone is in the range of 2 mg to 4 mg.

3. A method according to claim 2 wherein the daily amount of drospirenone is 3 mg.

4. A method according to claim 1 wherein ethinylestradiol and drospirenone are administered daily and uninterruptedly for 84 days followed by 7 days of non administration.

5. A method according to claim 1 wherein the uninterrupted administration of ethinylestradiol and drospirenone is for more than 110 days.

6. A method for reducing dysmenorrhea by administering 20 µg of ethinylestradiol and 2 mg to 4 mg of drospirenone, daily and uninterruptedly for at least 42 days.

7. A method for reducing dysmenorrhea by administering 20 µg of ethinylestradiol and 3 mg of drospirenone, daily and uninterruptedly for at least 42 days.

8. A method according to claim 6 wherein the uninterrupted administration is for more than one year.

* * * * *